ns on the benzene nucleus, $\beta$-(2,5-di-lower alkoxyphenyl)acryloni-
United States Patent [19]

Imai

[11] 3,992,449

[45] Nov. 16, 1976

[54] 2-(γ-AMINOPROPYL)HYDROQUINONES AND PROCESS FOR PRODUCING THE SAME

[75] Inventor: Shinichi Imai, Minami-ashigara, Japan

[73] Assignee: Fuji Photo Film Co., Ltd., Minami-ashigara, Japan

[22] Filed: Nov. 18, 1974

[21] Appl. No.: 524,836

[30] Foreign Application Priority Data

Nov. 16, 1973 Japan .............................. 48-128987

[52] U.S. Cl. .......................... 260/570.8 R; 96/66 R; 260/465 F
[51] Int. Cl.² .................. C07C 91/34; C07C 93/14; C07C 121/75
[58] Field of Search ................... 260/570.8 R, 570.8

[56] References Cited
UNITED STATES PATENTS
2,949,359   8/1960   Blout et al. ...................... 260/570.8

*Primary Examiner*—Lewis Gotts
*Assistant Examiner*—Dolph A. Torrence
*Attorney, Agent, or Firm*—Sughrue, Rothwell, Mion, Zinn & Macpeak

[57] ABSTRACT

1-(γ-Aminopropyl)-2,5-dihydroxybenzene and derivatives thereof having additional substituents on the benzene nucleus, $\beta$-(2,5-di-lower alkoxyphenyl)acrylonitriles and derivatives thereof having additional substituents on the benzene nucleus, and γ-aminopropyl-2,5-di-lower alkoxybenzenes and derivatives thereof having additional substituents on the benzene nucleus and a process for producing 1-(γ-aminopropyl)-2,5-dihydroxybenzene or derivatives thereof having additional substituents on the benzene nucleus which comprises reacting a 2,5-di-lower alkoxybenzaldehyde or a derivative thereof having additional substituents on the benzene nucleus in the 3-, 4- and/or 6-positions (wherein the substituents can be one or more of an alkyl group of 5 or less carbon atoms or a halogen atom) with cyanoacetic acid or an ester thereof to form a $\beta$-(2,5-di-lower alkoxyphenyl)acrylonitrile or a derivative thereof having additional substituents on the benzene nucleus, catalytically reducing the product, with or without previously isolating the product, to form a γ-aminopropyl-2,5-di-lower alkoxybenzene or a derivative thereof having additional substituents on the benzene nucleus, and then dealkylating the product obtained in the reduction, with or without previously isolating the product.

18 Claims, No Drawings

2-(γ-AMINOPROPYL)HYDROQUINONES AND PROCESS FOR PRODUCING THE SAME

BACKGROUND OF THE INVENTION

1. FIELD OF THE INVENTION

This invention relates to novel β-(2,5-di-lower alkoxyphenyl)acrylonitrile and derivatives thereof having additional substituents on the benzene nucleus, as well as a process for the production thereof.

This invention also relates to novel γ-aminopropyl-2,5-di-lower alkoxybenzene and derivatives thereof having additional substituents on the benzene nucleus, as well as a process for the production thereof.

This invention further relates to a novel 1-(γ-aminopropyl)-2,5-dihydroxybenzene and derivatives thereof having additional substituents on the benzene nucleus, as well as a process for the production thereof.

2. DESCRIPTION OF THE PRIOR ART

As compounds similar to the 1-(γ-aminopropyl)-2,5-dihydroxybenzene and derivatives thereof having additional substituents on the benzene nucleus, hitherto 2-(β-aminoethyl)hydroquinone and 2-(β-aminopropyl)hydroquinone have been are already known.

However, a dye developing agent produced by way of 2-(β-aminoethyl)hydroquinone as an intermediate has extremely poor solubility and, therefore, can not be practically used at all. Moreover, the intermediate can be prepared by synthesizing 2,5-dimethoxy-β-nitrostyrene from 2,5-dimethoxybenzaldehyde and nitromethane and then subjecting the same to a reduction and demethylation, but the process is disadvantageous in that the reaction is difficult to operate and the yield is quite low.

On the other hand, while 2-(β-aminopropyl)hydroquinone is useful as an intermediate for a dye developing agent, the production thereof is disadvantageous in that the reaction is difficult to operate and the yield is low. (2-(β-aminopropyl)hydroquinone can be prepared, for example, by synthesizing 1-(2',5'-dimethoxyphenyl)-2-nitro-1-propene from 2,5-dimethoxybenzaldehyde and nitroethane and then subjecting the same to a reduction and demethylation.)

SUMMARY OF THE INVENTION

Therefore, an object of this invention is to provide 1-(γ-aminopropyl)-2,5-dihydroxybenzene and derivatives thereof having additional substituents on the benzene nucleus which are useful hydroquinone derivatives, as well as a process for the production thereof in which the reaction can be easily operated and the yield is high.

Another object of this invention is to provide β-(2,5-di-lower alkoxyphenyl)acrylonitrile and derivatives thereof having additional substituents on the benzene nucleus which are useful as a raw material for the production of the above compounds, as well as a process for the production thereof.

A further object of this invention is to provide γ-aminopropyl-2,5-di-lower alkoxybenzene and derivatives thereof having additional substituents on the benzene nucleus which are useful as a raw material for the production of the above hydroquinone compounds, as well as a process for the production thereof.

Accordingly, this invention provides dialkoxy- or dihydroxy-substituted benzene derivatives represented by the general formula (I),

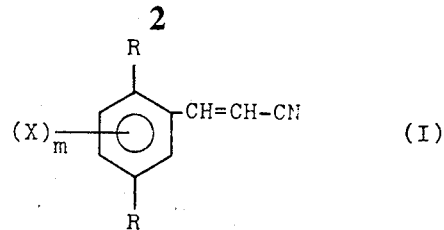

wherein R may be the same or different and represents a lower-alkoxy group having up to 5 carbon atoms such as a methoxy, ethoxy, propoxy, iso-propoxy, butoxy, or pentyloxy group, X represents a lower-alkyl group having up to 5 carbon atoms such as a methyl, ethyl, propyl, iso-propyl, butyl, or pentyl group or a halogen atom such as a chlorine or bromine atom, and m is an integer of from 0 to 3;

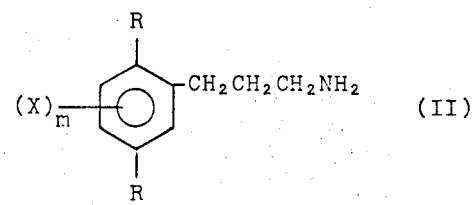

wherein R, X and $m$ are as defined above; and

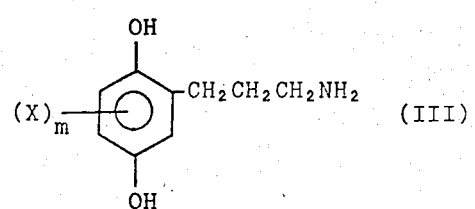

wherein X and $m$ are as defined above.

In another embodiment of this invention, this invention provides an effective process for producing the above-described dihydroxy substituted benzene derivatives of the general formula (III) (or dialkoxy substituted benzene derivatives of the general formulas (I) and (II) as intermediates) which comprises reacting a 2,5-di-lower alkoxy(methoxy, ethoxy, etc.)-benzaldehyde or a derivative thereof having additional substituents on the benzene nucleus in the 3-, 4- and/or 6-positions (wherein the substituents can be one or more of an alkyl group of 5 or less carbon atoms or a halogen atom) with cyanoacetic acid or a lower alkyl ester thereof (for example, the methyl ester, the ethyl ester, etc.) to form a β-(2,5-di-lower alkoxyphenyl)acrylonitrile or a derivative thereof having additional substituents on the benzene nucleus, catalyticly reducing the β-(2,5-di-lower alkoxyphenyl)acrylonitrile or the derivative thereof to form a γ-aminopropyl-2,5-di-lower alkoxybenzene or a derivative thereof having additional substituents on the benzene nucleus and then dealkylating the γ-aminopropyl-2,5-di-lower alkoxybenzene or a derivative thereof.

DETAILED DESCRIPTION OF THE INVENTION

The finding of this invention is surprising since compounds of this type have been produced using various methods which depend upon the particular compounds being produced and there is no so-called general method which is common to these compounds. In addition, the above hydroquinone and derivatives thereof having additional substituents on the benzene nucleus themselves, as well as a process for the production thereof are not known.

The position of an amino group on the side chain of the benzene nucleus, whether it is present on a therminal or other position than the terminal position, influences the reactivity and the solubility. In this connection, the compounds produced according to this invention are very useful as compared with other similar compounds in regard to the reactivity in forming a polymer effective as an antioxidant by reacting the compound with a polymer containing a maleic anhydride unit in the structure, and the solubility in using the compound as an additive for a photographic emulsion, the additive being formed by reacting the amino group with any other group.

More specifically, 2-(γ-aminopropyl)hydroquinone and derivatives thereof having additional substituents on the benzene nucleus are useful as a developing agent for a silver halide photographic light-sensitive material or an intermediate therefor (for example, for a dye developing agent), as a raw material for producing a polymer having oxidation inhibiting property through reaction with a polymer containing a maleic anhydride unit, as a general antioxidant or an intermediate therefor and as intermediates for dyes and drugs.

The β-(2,5-di-lower alkoxyphenyl)acrylonitrile or derivatives thereof having additional substituents on the benzene nucleus can be readily prepared by heating 2,5-di-lower alkoxybenzaldehyde or a derivative thereof having additional substituents on the benzene nucleus with cyanoacetic acid or an ester thereof in the presence of a basic decarboxylation catalyst (for example, nitrogen-containing heterocyclic compounds (aromatic compounds or saturated compounds thereof such as pyridine, piperidine, morpholine, quinoline or picoline)). The decarboxylation catalyst can be used in an amount broadly ranging from several drops to a large excess, and, where a large excess is used, the catalyst can also serve as a solvent. A suitable amount of the catalyst can range from about 0.02 to 5 times, preferably 0.03 to 3.5 times by weight to the weight of the 2,5-di-lower alkoxybenzaldehyde or derivative thereof. In the above process of this invention, it is not essential to use a solvent, but an organic solvent capable of dissolving the above aldehyde and cyanoacetic acid or ester thereof can be used, if desired. Such solvents preferably simultaneously act as a basic catalyst. For example, the method of using pyridine as a solvent and adding a small amount of piperidine can provide an end product in high yield (about 80 to 90%). Suitable solvents include heterocyclic compounds containing a nitrogen atom as a hetero-atom, such as pyridine, picoline, and the like aromatic hydrocarbons such as benzene, alcohols such as methanol, ethanol, propanol and the like, carboxylic acid esters such as ethyl acetate, butyl acetate and the like, ethers such as diethyl ether, tetrahydrofuran and the like. A suitable amount of the solvent ranges from about 2 to 5 times by weight to the weight of the 2,5-di-lower alkoxybenzaldehyde or derivative thereof.

The 2,5-di-lower alkoxybenzaldehyde or a derivative thereof having additional substituents on the benzene nucleus and cyanoacetic acid or cyanoacetic acid ester are suitably added in an approximately equal molar ratio or with an excess, and preferably in a molar ratio of about 1:1 to 1:5.

In using cyanoacetic acid, the reaction is generally carried out at about 60° to 80° C for about 1 to 2 hours and then at an elevated temperature of about 150° to 180° C for about 4 to 5 hours.

However, in the process of this invention, the temperature and the time employed are not restricted only to the above ranges and they can be optionally selected outside the above ranges if the reduction of the reaction rate and the yield can be tolerated. Where an ester of cyanoacetic acid (e.g., having 1 to 4 carbon atoms in the alkyl moiety, for example, the ethyl ester or the methyl ester) is used in place of cyanoacetic acid, the process is generally conducted in a manner such that the 2,5-di-lower alkoxybenzaldehyde or a derivative thereof having additional substituents on the benzene nucleus and the ester are reacted at temperatures ranging from about room temperature (e.g., about 20 to 30° C) to 100° C, preferably about 20° to 30° C, with or without a solvent (for example, aromatic hydrocarbons such as benzene, lower alcohols such as methanol or ethanol, esters such as ethyl acetate, or ethers such as diethyl ether, tetrahydrofuran or dioxane, e.g., in an amount of about 2 to 5 times by weight of the solvent to the weight of the 2,5-di-lower alkoxybenzaldehyde or derivative thereof) and the resulting ester derivative is subjected to hydrolysis, e.g., at a temperature of about 20° to 80° C, using an alkali such as potassium hydroxide or sodium hydroxide, e.g., in a molar amount of about 1:1 to 1:5 to the resulting ester derivative and then decarboxylated in the presence of a basic decarboxylation catalyst as described above (for example, pyridine - piperidine) to obtain the desired product in high yield (about 80 to 90%).

Thereafter, the resulting acrylonitrile derivative is catalyticly reduced in the presence of a catalyst such as Raney nickel, Raney cobalt, palladium-carbon or platinum (preferably, Raney nickel) and, if desired, in a solvent. A suitable amount of the catalyst can range from about 3 to 10% by weight to the weight of the acrylonitrile derivative. The solvent used can be the lower alcohols, esters, ethers or aromatic hydrocarbons described above (preferably, ethanol or methanol).

It is desirable in this reaction to use ammonia in an about equal molar amount or an excess based on the nitrile as the raw material (preferably, about 1 to about 12 times, preferably, 3 to 10 times, the molar amount of the nitrile) in order to prevent the formation of a secondary amine. The reaction can be carried out, for example, at about 50° to about 180° C, but the reaction is preferably carried out at about 80° to about 130° C for about 2 to about 4 hours in view of the reaction rate and the operation. The pressure of hydrogen gas supplied in the process preferably ranges from about 20 to 120 atm., particularly 50 to 80 atm.

1-($\gamma$-Aminopropyl)-2,5-dihydroxybenzene or the derivatives thereof having additional substituents on the benzene nucleus can be readily obtained by dealkylating $\gamma$-aminopropyl-2,5-di-lower alkoxybenzene or a derivative thereof having additional substituents on the benzene nucleus which has been formed through the catalytic reduction. The dealkylation readily proceeds using hydrohalic acids such as hydrochloric acid, hydrobromic acid or hydroiodic acid, salts of nitrogen-containing heterocyclic compounds, for example, hydrohalide salts such as pyridine-hydrochloride or picoline-hydrochloride, or the like, as described in U.S. Pat. Nos. 3,062,884 and 3,187,046. Hydrobromic acid is preferably used considering the easy reaction and the treatment after the reaction. The amount of the hydrobromic acid or hydroiodic acid is suitably about 5 to 15 times, preferably 7 to 10 times, by weight to the weight of the $\gamma$-aminopropyl-2,5-di-lower alkoxybenzene or derivative thereof in view of the reactivity and the treatment after the reaction.

The reaction proceeds at above about 100° C, e.g., about 100° to 200° C, and suitably at a temperature of about 140° to 180° C for about 2 to 4 hours. However, the reaction can be carried out under other conditions if the prolonged reaction time and the difficulties in after-treatment due to the coloring of the reaction product are permissible. A suitable amount of the dealkylation agent ranges from about 6 to 18 times, preferably 8 to 12 times, by weight to the weight of the $\gamma$-aminopropyl-2,5-di-lower alkoxybenzene or derivative thereof.

Specific examples of compounds which can be obtained according to this invention are set forth below without intending to limit this invention.

1. $\beta$-(2,5-Dimethoxy-3-methylphenyl)acrylonitrile
2. $\beta$-(2,5-Dimethoxyphenyl)acrylonitrile
3. $\beta$-(2,5-Dimethoxy-3-ethylphenyl)acrylonitrile
4. $\beta$-(2,5-Dimethoxy-3-t-butylphenyl)acrylonitrile
5. $\beta$-(2,5-Dimethoxy-3-bromophenyl)acrylonitrile
6. $\beta$-(2,5-Dimethoxy-3-chlorophenyl)acrylonitrile
7. $\beta$-(2,5-Dimethoxy-6-bromophenyl)acrylonitrile
8. $\beta$-(2,5-Diethoxyphenyl)acrylonitrile
9. $\beta$-(2,5-Diethoxy-3-methylphenyl)acrylonitrile
10. $\beta$-(2,5-Diethoxy-3-ethylphenyl)acrylonitrile
11. $\beta$-(2,5-Diethoxy-3-t-butylphenyl)acrylonitrile
12. $\beta$-(2,5-Diethoxy-3-bromophenyl)acrylonitrile
13. $\beta$-(2,5-Diethoxy-3-chlorophenyl)acrylonitrile
14. $\beta$-(2,5-Diethoxy-6-bromophenyl)acrylonitrile
1'. $\gamma$-Aminopropyl-2,5-dimethoxybenzene
2'. $\gamma$-Aminopropyl-2,5-dimethoxy-3-methylbenzene
3'. $\gamma$-Aminopropyl-2,5-dimethoxy-3-ethylbenzene
4'. $\gamma$-Aminopropyl-2,5-dimethoxy-3-t-butylbenzene
5'. $\gamma$-Aminopropyl-2,5-dimethoxy-3-butylbenzene
6'. $\gamma$-Aminopropyl-2,5-dimethoxy-3-chlorobenzene
7'. $\gamma$-Aminopropyl-2,5-dimethoxy-6-bromobenzene
8'. $\gamma$-Aminopropyl-2,5-diethoxybenzene
9'. $\gamma$-Aminopropyl-2,5-diethoxy-3-methylbenzene
10'. $\gamma$-Aminopropyl-2,5-diethoxy-3-ethylbenzene
11'. $\gamma$-Aminopropyl-2,5-diethoxy-3-t-butylbenzene
12'. $\gamma$-Aminopropyl-2,5-diethoxy-3-bromobenzene
13'. $\gamma$-Aminopropyl-2,5-diethoxy-3-chlorobenzene
14'. $\gamma$-Aminopropyl-2,5-diethoxy-6-bromobenzene
1''. 1-($\gamma$-Aminopropyl)-2,5-dihydroxybenzene
2''. 1-($\gamma$-Aminopropyl)-2,5-dihydroxy-3-methylbenzene
3''. 1-($\gamma$-Aminopropyl)-2,5-dihydroxy-3-ethylbenzene
4''. 1-($\gamma$-Aminopropyl)-2,5-dihydroxy-3-t-butylbenzene
5''. 1-($\gamma$-Aminopropyl)-2,5-dihydroxy-3-bromobenzene
6''. 1-($\gamma$-Aminopropyl)-2,5-dihydroxy-3-chlorobenzene
7''. 1-($\gamma$-Aminopropyl)-2,5-dihydroxy-6-bromobenzene This invention will be described in greater detail by reference to the following examples. Unless otherwise indicated, all parts, percents, ratios and the like are by weight.

EXAMPLE 1

Synthesis of $\beta$-(2,5-Dimethoxyphenyl)acrylonitrile

A mixture of 166 g of 2,5-dimethoxybenzaldehyde, 76 g of cyanoacetic acid, 5 ml of piperidine and 400 ml of pyridine was heated at 80° C under stirring for 2 hours and then refluxed with heating at 140° C for 5 hours. After the reaction, the mixture was cooled to room temperature and poured into 2 liters of ice water. The precipitated crystals were filtered out and recrystallized from ethanol to give 117 g of the end product having a melting point of 70 ~ 71° C (yield 62%).

EXAMPLE 2

Synthesis of $\gamma$-Aminopropyl-2,5-dimethoxybenzene 90 g of $\beta$-(2,5-Dimethoxyphenyl)acrylonitrile and 500 ml of ethanol containing about 100 g of ammonia were subjected to catalytic reduction in the presence of Raney nickel under a hydrogen pressure of 80 atm. and at 130° C for 3 hours. After the reaction, distillation under reduced pressure gave 82 g of the end product having a boiling point of 105° ~ 107° C/l mmHg (yield 88.2%).

EXAMPLE 3

Synthesis of $\gamma$-Aminopropylhydroquinone.hydrobromide 100 g of $\gamma$-aminopropyl-2,5-dimethoxybenzene was heated at an oil bath temperature of 180° C in 830 ml of 48% hydrobromic acid while blowing therein nitrogen gas. After the reaction, the reaction mixture was cooled, and the precipitated crystals were filtered out and dried to obtain 88 g of the end product having a melting point of 130° ~ 131° C (yield 69.3%).

While the invention has been described in detail and with reference to specific embodiments thereof, it will be apparent to one skilled in the art that various changes and modifications can be made therein without departing from the spirit and scope thereof.

What is claimed is:

1. A γ-aminopropyl-2,5-di-lower alkoxybenzene or a derivative thereof having additional substituents on the benzene nucleus in the 3-, 4- and/or 6-position wherein the substituents can be one or more of an alkyl group having 5 or less carbon atoms or a halogen atom.

2. The γ-aminopropyl-2,5-di-lower alkoxybenzene or a derivative thereof of claim 1, wherein said di-lower alkoxy moiety is a methoxy, ethoxy, propoxy, iso-propoxy, butoxy, or pentoxy moiety, wherein said alkyl group having 5 or less carbon atoms is a methyl, ethyl, propyl, iso-propyl, butyl, or pentyl group and wherein said halogen atom is a chlorine or bromine atom.

3. A 1-(γ-aminopropyl)-2,5-dihydroxybenzene or a derivative thereof having additional substituents on the benzene nucleus in the 3-, 4- and/or 6-position wherein the substituents can be one or more of an alkyl group having 5 or less carbon atoms or a halogen atom.

4. The 1-(γ-aminopropyl)-2,5-dihydroxybenzene or a derivative thereof of claim 3, wherein said alkyl group having 5 or less carbon atoms is a methyl, ethyl, propyl, iso-propyl, butyl, or pentyl group and wherein said halogen atom is a chlorine or bromine atom.

5. A process for producing the γ-aminopropyl-2,5-di-lower alkoxybenzene or a derivative thereof of claim 1, which comprises reacting at 2,5-di-lower alkoxybenzaldehyde or a derivative thereof having additional substituents on the benzene nucleus in the 3-, 4- and/or 6-position wherein the substituents can be one or more of an alkyl group having 5 or less carbon atoms or a halogen atom with cyanoacetic acid or a lower alkyl ester thereof in the presence of a basic decarboxylation catalyst to form a β-(2,5-di-lower alkoxyphenyl)acrylonitrile or a derivative thereof having additional substituents on the benzene nucleus and catalyticly reducing the β-(2,5-di lower alkoxyphenyl)acrylonitrile or a derivative thereof having additional substituents on the benzene nucleus with hydrogen in the presence of ammonia to form said γ-aminopropyl-2,5-di-lower alkoxybenzene or a derivative thereof having additional substituents on the benzene nucleus.

6. The process of claim 5, wherein the molar ratio of the 2,5-di-lower alkoxybenzaldehyde or the derivative thereof having additional substituents on the benzene nucleus to ammonia ranges from about 1:1 to 1:12 and the hydrogen is employed at a pressure of about 20 to 120 atmospheres.

7. The process of claim 5, wherein said process is conducted in a solvent.

8. The process of claim 7, wherein said solvent is an alcohol, a carboxylic acid ester, an ether, or an aromatic hydrocarbon.

9. The process of claim 7, wherein said catalytically reducing is with a Raney nickel catalyst, a Raney cobalt catalyst, a palladium-carbon catalyst or platinum black.

10. The process of claim 9, wherein said catalyticly reducing is with Raney nickel.

11. The process of claim 5, wherein said reducing is at a temperature ranging from about 50° to 180° C.

12. A process for producing the 1-(γ-aminopropyl)-2,5-dihydroxybenzene or a derivative thereof of claim 3 which comprises reacting a 2,5-di-lower alkoxybenzaldehyde or a derivative thereof having additional substituents on the benzene nucleus in the 3-, 4- and/or 6-position wherein the substituents can be one or more of an alkyl group having 5 or less carbon atoms or a halogen atom with cyanoacetic acid or a lower alkyl ester thereof in the presence of a basic dicarboxylation catalyst to form a β-(2,5-di-lower alkoxyphenyl)acrylonitrile or a derivative thereof having additional substituents on the benzene nucleus, catalyticly reducing the β-(2,5-di-lower alkoxyphenyl)acrylonitrile or a derivative thereof having additional substituents on the benzene nucleus with hydrogen in the presence of ammonia to form a γ-aminopropyl-2,5-di-lower alkoxybenzene or a derivative thereof having additional substituents on the benzene nucleus, and then dealkylating the γ-aminopropyl-2,5-di-lower alkoxybenzene or a derivative thereof having additional substituents on the benzene nucleus.

13. The process of claim 12, wherein said dealkylating is with a hydrohalic acid, or a salt of a nitrogen-containing heterocyclic compound.

14. The process of claim 13, wherein said hydrohalic acid is hydrochloric acid, hydrobromic acid, or hydroiodic acid and wherein said salt of said nitrogen-containing heterocyclic compound is picoline-hydrochloride or pyridine-hydrochloride.

15. The process of claim 12, wherein said dealkylating is at a temperature of about 140° to 180° C.

16. The process of claim 15, wherein said dealkylating is in the presence of an inert gas.

17. The process of claim 16, wherein said dealkylating is with hydrobromic acid or hydroiodic acid.

18. The process of claim 17, wherein said hydrobromic acid or said hydroiodic acid is present in an amount of about 5 to 15 times by weight to the weight of said di-lower alkoxybenzene compound or the derivative thereof having additional substituents on the benzene nucleus.

* * * * *